United States Patent
Rahul et al.

(10) Patent No.: US 8,076,483 B2
(45) Date of Patent: Dec. 13, 2011

(54) PROCESS FOR THE PREPARATION OF PURE RISEDRONIC ACID OR SALTS

(75) Inventors: Saxena Rahul, Chandigarh (IN); Jain Anshul Kumar, Chandigarh (IN); Srinivasan Chidambaram Venkateswaran, Panchkula (IN); Wadhwa Lalit, Panchkula (IN)

(73) Assignee: M/s. Ind Swift Laboratories Limited, Chandigarh (IN)

( * ) Notice: Subject to any disclaimer, the term of this patent is extended or adjusted under 35 U.S.C. 154(b) by 132 days.

(21) Appl. No.: 12/299,615

(22) PCT Filed: May 9, 2007

(86) PCT No.: PCT/IN2007/000187
§ 371 (c)(1),
(2), (4) Date: Nov. 5, 2008

(87) PCT Pub. No.: WO2007/132478
PCT Pub. Date: Nov. 22, 2007

(65) Prior Publication Data
US 2009/0182147 A1 Jul. 16, 2009

(30) Foreign Application Priority Data
May 11, 2006 (IN) .......................... 1177/DEL/2006

(51) Int. Cl.
C07F 9/06 (2006.01)
A61K 31/66 (2006.01)
(52) U.S. Cl. ........................................ 546/22; 514/102
(58) Field of Classification Search ................. 546/344
See application file for complete search history.

(56) References Cited

U.S. PATENT DOCUMENTS

| | | | |
|---|---|---|---|
| 5,583,122 A | 12/1996 | Benedict et al. | |
| 5,648,491 A | 7/1997 | Dauer et al. | |
| 5,908,959 A | 6/1999 | Kubela et al. | |
| 6,410,520 B2 | 6/2002 | Cazer et al. | |
| 6,562,974 B2 | 5/2003 | Cazer et al. | |
| 7,002,014 B2 | 2/2006 | Godlewski | |
| 7,038,083 B2 | 5/2006 | Lidor-Hadas et al. | |
| 7,276,604 B2 | 10/2007 | Richter et al. | |
| 7,332,603 B2 | 2/2008 | Deferra et al. | |
| 7,358,360 B2 | 4/2008 | Lifshitz-Liron et al. | |
| 7,361,761 B2 | 4/2008 | Senthikumar et al. | |
| 7,411,087 B2 * | 8/2008 | Patel et al. | 562/13 |
| 7,872,144 B2 | 1/2011 | Pandey et al. | |
| 2003/0195170 A1 | 10/2003 | Aronhime et al. | |
| 2004/0043967 A1 | 3/2004 | Lidor-Hadas et al. | |
| 2005/0215793 A1 | 9/2005 | Turchetta et al. | |
| 2006/0122395 A1 | 6/2006 | Neu et al. | |
| 2006/0128960 A1 | 6/2006 | Lidor-Hadas et al. | |
| 2006/0258625 A1 | 11/2006 | Deshpande et al. | |
| 2007/0112197 A1 | 5/2007 | Grassi et al. | |
| 2007/0142332 A1 | 6/2007 | Richter et al. | |
| 2007/0142636 A1 | 6/2007 | Mandava et al. | |
| 2007/0173484 A1 | 7/2007 | Divvela et al. | |
| 2007/0173645 A1 | 7/2007 | Danda et al. | |
| 2008/0194525 A1 | 8/2008 | Serrano et al. | |
| 2008/0300408 A1 | 12/2008 | Pandey et al. | |
| 2009/0198062 A1 | 8/2009 | Gore et al. | |
| 2009/0281320 A1 | 11/2009 | Dembkowski et al. | |
| 2009/0326227 A1 | 12/2009 | Baptista et al. | |
| 2010/0010258 A1 | 1/2010 | Bartl | |
| 2010/0016592 A1 | 1/2010 | Kim et al. | |
| 2010/0121066 A1 | 5/2010 | Ankush et al. | |
| 2010/0317859 A1 | 12/2010 | Kumar et al. | |

FOREIGN PATENT DOCUMENTS

| | | |
|---|---|---|
| WO | 03097655 | * 11/2003 |
| WO | WO 03/093282 | 11/2003 |
| WO | WO 2005/044831 | 5/2005 |
| WO | WO 2005/063779 | 7/2005 |
| WO | WO 2005/066190 | 7/2005 |
| WO | WO 2005/075487 | 8/2005 |
| WO | WO 2006/051553 | 5/2006 |
| WO | WO 2006/071128 | 7/2006 |
| WO | WO 2006/129056 | 12/2006 |
| WO | WO 2006/134603 | 12/2006 |
| WO | WO 2007/026379 | 3/2007 |
| WO | WO 2007/036688 | 4/2007 |
| WO | WO 2007/042048 | 4/2007 |
| WO | WO 2007/132138 | 11/2007 |

(Continued)

OTHER PUBLICATIONS

Kieczykowski et. al., "Preparation of (4-Amino-1-hydroxybutylidene)bisphosphonic Acid Sodium Salt, MK-217 (Alendronate Sodium). An Improved Procedure for the Preparation of 1-Hydroxy-1,1-bisphosphonic Acids", 1995, 60, pp. 8310-8312.*

(Continued)

*Primary Examiner* — Janet Andres
*Assistant Examiner* — Heidi Reese
(74) *Attorney, Agent, or Firm* — Law Office of Albert Wai-Kit Chan, PLLC

(57) ABSTRACT

The present invention relates to an industrially advantageous process of making bisphosphonic acid or its salt in particular risedronic acid, [1-hydroxy-2(3-pyridinyl)ethylidene]bisphosphonic acid, having formula-(I) or its salts in high purity and high yields.

(I)

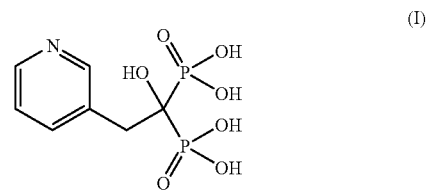

4 Claims, No Drawings

FOREIGN PATENT DOCUMENTS

| | | |
|---|---|---|
| WO | WO 2008/004000 | 1/2008 |
| WO | WO 2008/044245 | 4/2008 |
| WO | WO 2008/065542 | 6/2008 |
| WO | WO 2008/075831 | 6/2008 |
| WO | WO 2009/003001 A2 | 12/2008 |
| WO | WO 2009/034580 A1 | 3/2009 |
| WO | WO 2009/072769 A2 | 6/2009 |
| WO | WO 2011/023280 A1 | 3/2011 |

OTHER PUBLICATIONS

Kieczykowski, G.R., et al., 1995, "Preparation of (4-Amino-1-Hydroxybutylidene)bisphosphonic Acid Sodium Salt, MK-217 (Alendronate Sodium). An Improved Procedure for the Preparation of 1-Hydroxy-1,1-bisphosphonic acids," The Journal of Organic Chemistry, 60(25): 8310-8312.

\* cited by examiner

PROCESS FOR THE PREPARATION OF PURE RISEDRONIC ACID OR SALTS

This application is the National Stage of International Application PCT/IN2007/000187, filed May 9, 2007, which claims priority of Indian Application No. 1177/DEL/2006, filed May 11, 2006, which is hereby incorporated in its entirety b reference into this application.

FIELD OF INVENTION

The present invention relates to a process for the preparation of bisphosphonic acid in particular risedronic acid or its pharmaceutically acceptable salt, useful in the treatment of bone disorders. More particularly, the present invention relates to a novel method for the preparation of risedronic acid, namely, [1-hydroxy-2(3-pyridinyl)ethylidene]bisphosphonic acid having Formula-I or its salts in high purity and high yield.

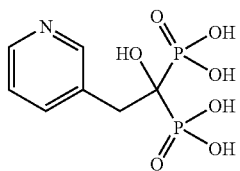

Formula-I

BACKGROUND OF THE INVENTION

The bisphosphonates, which are salts of bisphosphonic acids, are an important class of medicaments useful in the treatment of bone disorders such as Paget's disease and osteoporosis.

The bisphosphonates, for example etidronate, pamidronate, and risedronate are used in the form of various non-toxic and pharmaceutically acceptable esters, alkali metal salts and salts of alkaline-earth metals and their various hydrates. The form of the substance can have a fundamental influence on its solubility and its biological availability. The preferred forms of risedronate are the sodium and calcium salts.

Risedronic acid, chemically known as [1-hydroxy-2(3-pyridinyl)ethylidene]bisphosphonic acid, presently marketed as risedronate sodium under the tradename Actonel, is an important active pharmaceutical ingredient for the treatment of osteoporosis.

Risedronic acid and its pharmaceutically acceptable salts were first disclosed in U.S. Pat. No. 5,583,122. U.S. Pat. No. 5,583,122 discloses risedronic acid, but its preparation is not exemplified. On the contrary, the patent discloses the synthesis of an isomer, 1-hydroxy-2-(2-pyridyl)-1,1-diphosphonic acid, by reaction of (2-pyridyl) acetic acid with phosphorous acid and phosphorus trichloride in chlorobenzene. At the end of the reaction, the mixture solidifies and the solvent is removed by decantation.

But as described, when the reaction is carried out in chlorobenzene as a diluent, it does not solubilize the reaction components. The reaction starts as a two phase system, in which the melt gradually thickens into a non-stirrable mass. This semisolid sticky mass finally turns into a hard, rigid material coated on the walls of the reaction vessel which is preventing smooth heat transfer. The process might be suitable for laboratory preparation of gram quantities of the product; however, for industrial production it is not acceptable and is not reasonable even for a modest scale up.

U.S. Pat. No. 5,908,959 teaches use of long chain glycols to attempt to prevent the solidification of the reaction mixture, however the solidification cannot be totally avoided and these glycols cannot be recycled as they get converted to their corresponding chloride derivatives, which could be potentially toxic.

U.S. Pat. No. 5,648,491 discloses the use of methanesulfonic acid as reaction solvent. However, this technique involves the risk of safety as this solvent gives rise to uncontrollable reactions in the reaction conditions, when the temperature of the reacting mixture exceeds 85° C. Also, methanesulfonic acid is corrosive to skin, irritant and quite expensive.

U.S. Pat. No. 6,562,974 discloses a process for the preparation of geminal bisphosphonate using pyridine hydrochloride, morpholine hydrochloride & phosphoric acid at 70° C.

US Patent application 2004/0043967A1 discloses a process for the preparation of risedronate comprising the use of aromatic hydrocarbon or a silicone fluid optionally with polyalkene glycol. However, these solvents have a high cost and are difficult to eliminate from the finished product because of their high boiling point. Also, large quantities of poly-alkene glycol are required for the reaction, making it inefficient for use on a large scale.

PCT application WO 03/93282A1 describes a process for the preparation of risedronate & its monovalent cation using ionic liquid (tri-butyl ammonium chloride) as solvent at 15-120° C. The disclosed invention uses a solvent which is an expensive reagent, difficult to recover. Also, the yields reported are very low.

PCT application WO 05/044831A2 describes a process for the preparation of risedronic acid by using sulfolane as reaction solvent. Quenching of the reaction mixture containing sulfolane, with water causes high exothermicity and reaction becomes uncontrollable, hence is difficult to handle.

PCT application WO05/63779A2 describes a process for the preparation of risedronate using a mixture of phosphorous acid & phosphorous chloride in the absence of solvent. Requirement of more reaction time and large quantities of reactants for the reaction makes the process inefficient and expensive for use on a large scale. Also, the yields obtained are very low.

It is evident from prior art that different processes known for the preparation of risedronic acid and its pharmaceutically acceptable salts have some disadvantages associated with their use. So, there is an urgent need to develop a process for the preparation of risedronic acid or its salts that may overcome the drawbacks of prior art processes and should be industrially viable.

Accordingly, it is an object of the present invention to provide an efficient, safe and convenient process for preparation of risedronic acid wherein a water miscible neutral solvent such as acetonitrile is used and is further converted to risedronic acid monosodium salt in high yield and purity

SUMMARY OF THE PRESENT INVENTION

The present invention provides an industrially advantageous process for preparation of risedronic acid or salts, chemically known as [1-hydroxy-2(3-pyridinyl)ethylidene] bisphosphonic acid, of formula-I in high purity and high yields.

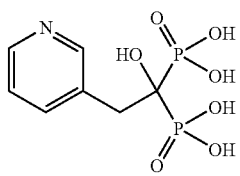

Formula-I

More particularly, the present invention provides improved processes for preparing risedronic acid and risedronic acid monosodium salt.

In one embodiment of the present invention, risedronic acid or salts preferably monosodium salt can be prepared by one pot process comprising reacting carboxylic acid compound in particular 3-pyridyl acetic acid with phosphorous acid in the presence of phosphorous halide in a water miscible neutral solvent such as acetonitrile, optionally distilling the solvent, quenching the reaction mixture with water, adjusting the pH using sodium source and isolating pure risedronic acid monosodium salt in high yield and purity.

In another embodiment, the present invention provides an efficient, economic and also environmentally friendly process which comprises obtaining the risedronic acid by reacting carboxylic acid compound in particular 3-pyridyl acetic acid with phosphorous acid in the presence of phosphorous halide in a water miscible neutral solvent such as acetonitrile, optionally distilling the solvent, quenching the reaction mixture with water. Thereafter risedronic acid is converted to risedronic acid mono sodium salt by the methods reported in the prior art.

Yet another embodiment of the present invention provides a process for the preparation of risedronic acid using chlorobenzene, avoiding decantation and isolation of the pure product by a simple layer separation method.

DETAILED DESCRIPTION OF THE INVENTION

The detailed description is provided herein to aid the persons skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

Accordingly, the present invention provides a process for the preparation of risedronic acid or salts of formula-I,

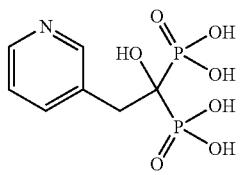

Formula-I by reacting a carboxylic acid in particular 3-pyridyl acetic acid of formula-II,

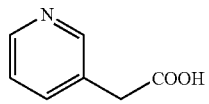

Formula-II with phosphorous acid and phosphorous halide in a suitable solvent like acetonitrile.

The present invention relates to a safe mode of preparing risedronic acid, in high yields and high purity. The present invention uses acetonitrile, which is a water miscible neutral solvent, relatively safe and inexpensive.

According to detailed embodiment of the present invention, 3-pyridyl acetic acid of formula II and the phosphorous acid in acetonitrile are reacted with phosphorous halide at temperature 40-80° C., and preferably at about 70-75° C. till phosphonylation is complete. Phosphorous halide can be selected from the group comprising phosphorous trichloride, phosphorous tribromide, phosphorous pentachloride, phosphorous pentabromide, phosphorous oxychloride, phosphorous oxybromide and the like.

Particularly, 3-pyridyl acetic acid of formula II and the phosphorous acid in acetonitrile are reacted with phosphorous trichloride. To the reaction mixture at temperature of about 70±5° C., phosphorous trichloride is added in small portions. The reaction mixture is refluxed to a temperature of 70±5° C. for a period of about 1 to about 12 hours till phosphonylation is complete. Optionally, acetonitrile is distilled off completely. The acetonitrile so recovered by distillation can be reused, thus making the process more economical and cost effective. The reaction mixture is quenched at ambient temperature with demineralized water.

In yet another embodiment of the present invention, to assist in impurity removal, it is effective to treat the substrate with an adsorbent, preferably with active charcoal. The filtered mass is further refluxed for a period of about 1 to about 12 hours at a temperature of 85±5° C. till complete hydrolysis. The reaction mixture is cooled to 0-5° C. and stirred for a period of 2-3 hours.

In a preferred embodiment of the present invention the risedronic acid is filtered and washed with demineralized water. Risedronic acid prepared can be optionally purified by acid base treatment like risedronic acid in water is treated with base to adjust pH above seven and further treatment with mineral acid to bring pH at 1-2.

It is observed that the process of the present invention provides risedronic acid in high yields and better quality as compared to any of the prior art processes. Thereafter risedronic acid is converted to risedronic acid monosodium salt by the methods reported in the prior art.

Particularly, the process for preparing risedronic acid monosodium salt comprises suspending the risedronic acid formed in demineralized water and pH is suitably adjusted to 4.2-4.5 with a base selected from alkali carbonates, alkali hydroxides or alkali bicarbonates. In the preferred embodiment of the present invention, the base employed is sodium hydroxide, preferably 50% sodium hydroxide. The precipitated salt may be isolated by a manner well known in art.

According to another embodiment, the present invention provides a one pot process for the preparation of risedronic acid mono sodium salt of formula-III,

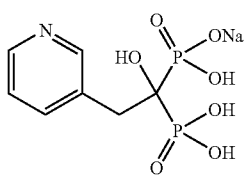

Formula-III by reacting carboxylic acid in particular 3-pyridyl acetic acid of formula-II,

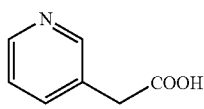

Formula-II with phosphorous acid and phosphorous halide in a suitable solvent, quenching the reaction with water and optionally distilling off the solvent, adjusting the pH using sodium source and isolating the highly pure risedronic acid monosodium salt in high yield and purity.

According to detailed embodiment of the present invention, 3-pyridyl acetic acid of formula II and the phosphorous acid are reacted in a suitable solvent like acetonitrile at reflux temperature. Phosphorous halide is slowly added to the above reaction mixture at a temperature of 40-10° C., preferably at about 7±5° C. till phosphonylation is complete. Phosphorous halide can be selected from amongst phosphorous trichloride, phosphorous tribromide, phosphorous pentachloride, phosphorous pentabromide, phosphorous oxychloride, phosphorous oxybromide and the like and preferably phosphorous trichloride is used.

When the phosphonylation is complete, the solvent is distilled off. As discussed earlier, distillation is not a must step here as presence of acetonitrile doesn't interferes with the course of the reaction.

After distillation, the filtered mass is cooled to ambient temperature preferably 25±2° C. and reaction mass is quenched with water. The resultant reaction mass is then charcoalised to decolorize the reaction mass.

The reaction mass is refluxed for a period of about 1 to 12 hours to complete hydrolysis. After hydrolysis, risedronic acid is converted to monosodium salt. The preparation of sodium salt is pH dependent, from about pH 3.0 to about pH 12.0. Preferably, the pH is adjusted to 4.3 to obtain the mono sodium salt using a suitable base.

The base can be selected from alkali carbonates, alkali hydroxides or alkali bicarbonates. In the preferred embodiment of the present invention, the base employed is sodium hydroxide and more preferably 50% sodium hydroxide.

The reaction can be further preceded in two ways. According to one embodiment of the present invention, the reaction mass is directly basified with sodium hydroxide at a pH of 4.2-4.5. According to another embodiment of the present invention, the reaction mass is first basified with sodium hydroxide at a pH of 8-9 and then acidified with concentrated hydrochloric acid to bring the pH to 4.2-4.5.

The reaction mass is initially cooled to ambient temperature and finally to a temperature of below 5° C. Thereafter the product can be isolated from the reaction mass by the methods known in prior alt such as filtration.

According to yet another embodiment of the present invention there is provided a process for the isolation of pure risedronic acid from the reaction mixture wherein 3-pyridyl acetic acid is reacted with phosphorous acid and phosphorous trichloride in chlorobenzene. acid in chlorobenzene are reacted with phosphorous trichloride at a suitable temperature, preferably at about 90±5° C. till phosphonylation is complete as reported in U.S. Pat. No. 5,583,122.

After completion of reaction, the reaction mixture is cooled to a temperature below 50° C. and demineralized water is added slowly. The reaction mass is stirred for a period of about 30 minutes and allow the layers to settle and separate. The organic layer is then extracted with demineralized water. The combined aqueous layer is charcoalised to decolorize the reaction mass. The filtered mass is refluxed azeotropically for a period of about 1 to 12 hours to complete hydrolysis and removal of traces of chlorobenzene. The reaction mass is then cooled to ambient temperature. Thereafter the product can be isolated from the reaction mixture by the methods known in prior art such as filtration. The product obtained is highly pure having purity greater than 97% by high performance liquid chromatography (HPLC) and yield is above 80%. Thus, layer separation method described in the present course of reaction overcomes the drawbacks of the prior art processes and hence provides an industrially reproducible route even by using chlorobenzene.

Major advantages realized in the present invention are increased process productivity and product purity. The process of the present invention is feasible commercially and simple on industrial scale. Direct conversion of 3-pyridyl acetic acid into risedronic acid monosodium salt without the isolation of risedronic acid results in reducing the time cycle of the reaction, avoiding complicated separation or purification steps and reducing expenditure on equipment, hence makes the process industrially advantageous and cost effective.

The present invention is further illustrated by the following examples which are provided merely to be exemplary of the inventions and is not intended to limit the scope of the invention. Certain modifications and equivalents will be apparent to those skilled in the art and are intended to be included within the scope of the present invention.

EXAMPLES

Example-1

Preparation of Risedronic Acid

3-Pyridine acetic acid (100 g) was added to acetonitrile (1.0 L). To the reaction mixture was added phosphorous acid (142 g). The reaction mass was heated up to reflux temperature (70-75° C.). To this phosphorous trichloride (271 g) was added slowly and the reaction mass was refluxed for 5.0 hours.

The solvent was distilled off completely under vacuum, Demineralized water (400 ml) was added to the reaction mass at ambient temperature and charcoalised. The filtered mass was refluxed for 4.0 hours at 85° C. The reaction mass was cooled to 0-5° C. and stirred for 2 hours. It was filtered and washed with demineralized water to get risedronic acid (175 g, yield 84.58%) as a white crystalline solid having purity of 98.59% by HPLC.

Example-2

Preparation of Risedronic Acid Monosodium Salt

3-Pyridine acetic acid (100 g) added to acetonitrile (1.0 L). To the reaction mixture was added phosphorous acid (142 g).

The reaction mass was heated up to reflux temperature (70-75° C.). To this phosphorous trichloride (271 g) was added slowly at 70° C. and the reaction mass was refluxed for 5.0 hours. The solvent was distilled off completely under vacuum. Demineralized water (400 ml) was added to the reaction mass at ambient temperature and charcoalised. The filtered mass was refluxed for 4.0 hours at 85° C. The reaction mass was cooled to 0-5° C. and stirred for 2 hours. It was filtered and washed with demineralized water to get risedronic acid as a white crystalline solid. The wet material was dissolved in demineralized water (300 ml) and 50% sodium hydroxide solution was added to reaction mass to make the pH basic, charcoalised and acidified with concentrated hydrochloric acid. The reaction mass was stirred further for 1.0 hour. The solid was filtered, washed with demineralized water to get the pure risedronic acid (160 g, yield 77.33%) having purity of 99.25% by HPLC.

Preparation of Risedronic Acid Mono Sodium Salt

3-Pyridine acetic acid (25 g) was added to acetonitrile (250 ml). To the reaction mixture was added phosphorous acid (35.5 g). The reaction mass was heated up to reflux temperature (70-75° C.). To this phosphorous trichloride (58.97 g) was added slowly and the reaction mass was refluxed for 5.0 hours. The solvent was distilled off completely under vacuum. Demineralized water (1.00 ml) was added to the reaction mass at ambient temperature and charcoalised. The filtered mass was refluxed for 4-5 hours at 85° C. The reaction mass was cooled to ambient temperature. 50% sodium hydroxide solution was added to reaction mass to make the pH basic, charcoalised and acidified with concentrated hydrochloric acid to pH 4.2-4.5. The reaction mass was cooled to ambient temperature and then to 0-5° C. and stirred further for 2.0 hour. The solid was filtered, washed with 20% aqueous ethyl alcohol to get the pure risedronate sodium (51 g) having purity of 99.66% by HPLC.

Example-4

Preparation of Risedronic Acid Mono Sodium Salt

3-Pyridine acetic acid (25 g) was added to acetonitrile (250 ml). To the reaction mixture was added phosphorous acid (35.5 g). The reaction mass was heated up to reflux temperature (70-75° C.). To this phosphorous trichloride (58.97 g) was added slowly and the reaction mass was refluxed for 5.0 hours. The solvent was distilled off completely under vacuum. Demineralized water (100 ml) was added to the reaction mass at ambient temperature and charcoalised. The filtered mass was refluxed for 4-5 hours at 85° C. The reaction mass was cooled to 50-60° C. 50% sodium hydroxide solution was added to reaction mass to make the pH 4.2-4.5. The reaction mass was cooled to ambient temperature and then to 0-5° C. and stirred further for 2.0 hour. The solid was filtered, washed with 20% aqueous ethyl alcohol to get the pure risedronate sodium (33 g) having purity of 99.24% by HPLC.

Example-5

Preparation of Risedronic Acid

3-Pyridine acetic acid (25 g) added to chlorobenzene (250 ml). To the reaction mixture was added phosphorous acid (35.50 g). The reaction mass was heated up to 85-90° C. To this phosphorous 95° C. and cooled to 25° C. To the reaction mass demineralized water was added slowly at ambient temperature. The reaction mass was stirred for 30 minutes. The layers were allowed to settle and separate. The organic layer was extracted with demineralized water (50 ml). The combined aqueous layer was charcoalised and the filtered mass was refluxed azeotropically for 12 hours. The reaction mass was cooled to ambient temperature, filtered and washed with demineralized water (50 ml) to get risedronic acid (41.5 g, yield 80.22%) having purity of 97.53% by HP Reference Example Preparation of Risedronic Acid 3-Pyridine acetic acid (25 g) in 500 ml of chlorobenzene added to phosphorous acid (35.5 g). The reaction mixture was heated up to 85-90° C. To the reaction mixture phosphorous trichloride (58.97 g) was added slowly to obtain a yellowish rigid, thick mass. The reaction mass was cooled to ambient temperature. The solvent was decanted. Demineralized water (200 ml) was added to the reaction mass and refluxed azeotropically, to remove residual chlorobenzene. Filtered through hyflo bed while hot, washed with hot demineralized water. The reaction mass was cooled to 0-5° C., stirred for 1.0 hour, filtered the solid and washed to get risedronic acid (30.0 g, yield 58%) having purity of 83.98% by HPLC.

The invention claimed is:

1. A process for the preparation of risedronic acid of Formula I,

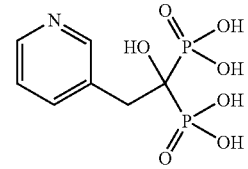

Formula-I

Comprising the steps of:
reacting carboxylic acid compound of Formula-II,

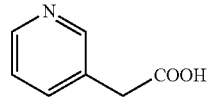

Formula-II with phosphorous acid and phosphorous halide in acetonitrile at a temperature of 40-80° C.;

distilling off reaction solvent completely;

quenching the resulting reaction mixture with water;

refluxing the reaction mixture for sufficient time to complete hydrolysis; and isolating the pure risedronic acid of Formula I.

2. The process of claim 1, wherein the phosphorous halide is selected from the group consisting of phosphorous trichloride, phosphorous tribromide, phosphorous pentachloride, phosphorous pentabromide, phosphorous oxychloride, and phosphorous oxybromide.

3. A process for the preparation of risedronic acid monosodium salt of Formula III,

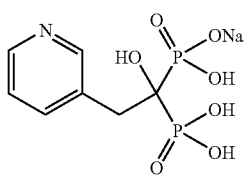

Formula-III comprising the steps of:
reacting carboxylic acid compound of Formula-II,

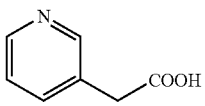

Formula-II with phosphorous acid and phosphorous halide in acetonitrile at a temperature of 40-80° C.;

distilling off reaction solvent completely;

quenching the resulting reaction mixture with water;

refluxing the reaction mixture for sufficient time to complete hydrolysis;

treating the reaction mixture with sodium hydroxide in water; and isolating risedronic acid mono-sodium salt of Formula III.

4. The process of claim 3, wherein the phosphorous halide is selected from the group consisting of phosphorous trichloride, phosphorous tribromide, phosphorous pentachloride, phosphorous pentabromide, phosphorous oxychloride, and phosphorous oxybromide.

* * * * *